United States Patent [19]
Miyagi et al.

[11] Patent Number: 6,015,810
[45] Date of Patent: Jan. 18, 2000

[54] AQUEOUS OPHTHALMIC SOLUTION CONTAINING APAFANT AS ACTIVE INGREDIENT

[75] Inventors: Syogo Miyagi; Mitsuaki Kuwano; Noriyuki Kunou, all of Osaka, Japan

[73] Assignee: Santen Pharmaceutical Co., Ltd., Osaka, Japan

[21] Appl. No.: 09/051,377

[22] PCT Filed: Oct. 9, 1996

[86] PCT No.: PCT/JP96/02933

§ 371 Date: Apr. 8, 1998

§ 102(e) Date: Apr. 8, 1998

[87] PCT Pub. No.: WO97/13517

PCT Pub. Date: Apr. 17, 1997

[30] Foreign Application Priority Data

Oct. 9, 1995 [JP] Japan .................................. 7-261337

[51] Int. Cl.⁷ .................................................. A67K 31/55
[52] U.S. Cl. .......................................... 514/220; 514/912
[58] Field of Search ..................... 514/220, 912

[56] References Cited

FOREIGN PATENT DOCUMENTS

| | | |
|---|---|---|
| 2024630 | 4/1991 | Canada . |
| 46-26986 | 8/1971 | Japan . |
| 62-277323 | 12/1987 | Japan . |
| 3-106826 | 5/1991 | Japan . |
| 3-128332 | 5/1991 | Japan . |
| 5-507467 | 10/1993 | Japan . |
| WO 90/01927 | 3/1990 | WIPO . |
| WO 91/18608 | 12/1991 | WIPO . |
| WO 93/07129 | 4/1993 | WIPO . |

OTHER PUBLICATIONS

Terashita et al, "Beneficial Effects of TCV–309, A Novel Potent and Selective Platelet Activating Factor Antagonist in Endotoxin and Anaphylactic Shock in Rodents", The Journal of Pharmacology and Experimental Therapeutics, vol. 260, No. 2, pp. 748–755 (1992).

Casals–Stenzel, "Protective Effect of Web 2086, A Novel Antagonist of Platelet Activating Factor, In Endotoxin Shock", European Journal of Pharmacology, vol. 135, pp. 117–122 (1987).

*Primary Examiner*—Zohreh Fay
*Attorney, Agent, or Firm*—Frishauf, Holtz, Goodman, Langer & Chick, P.C.

[57] ABSTRACT

The present invention relates to an aqueous ophthalmic solution containing apafant and additives wherein apafant is stabilized by lowering ionic strength to 0.05 or below, and a method of stabilizing apafant in the ophthalmic solution.

32 Claims, No Drawings

AQUEOUS OPHTHALMIC SOLUTION CONTAINING APAFANT AS ACTIVE INGREDIENT

This application is a 371 of PCT/JP96/02933 filed on Oct. 9, 1996.

FIELD OF THE INVENTION

The present invention relates to an aqueous ophthalmic solution containing apafant as an active ingredient and a method for attaining stabilization of apafant in the aqueous ophthalmic solution by lowering ionic strength (0.05 or below) depending on additives contained in the solution.

BACKGROUND ART

Apafant is a compound represented by a chemical name of 4-(2-chlorophenyl)-9-methyl-2-[3-(4-morpholinyl)-3-propanon-1-yl]-6H-thieno[3,2-f][1,2,4]-triazolo[4,3-a][1,4] diazepine (see the following structural formula [I]) and is known to exhibit a high antagonistic activity on a triazolo-diazepine platelet activating factor (hereinafter referred to as PAF) (Japanese Laid-open Patent Publication No. 176591/1986).

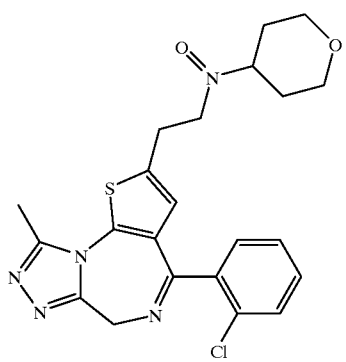

[I]

PAF is an inflammatory chemical mediator which has a very high physiological activity and is proved to participate in diseases such as inflammatory diseases (e.g. asthma, nephritis), disseminated intravascular coagulation syndrome and shock.

Various medicinal uses are already known regarding apafant, which has strong antagonism to PAF. For example, WO93/07129 discloses that apafant is useful as a therapeutic agent for osteoporosis because it has an inhibitory effect on absorption of bones. Japanese Laid-open Patent Publication No. 106826/1991 discloses that apafant is useful for cardiopathy such as heart failure because it was recognized to inhibit β-adrenoreceptor-mediated contraction decrease in hearts of rats whose spinae had been broken. WO90/01927 discloses that apafant is useful for autoimmune diseases because it was recognized to increase platelets in patients with idiopathic thrombocytopenic purpura. It was also reported that apafant increased survival rates concentration-dependently against anaphylactic shock (J. Pharmacol. Exp. Ther., 260, 748–755 (1992)) and exhibited antagonism to hypotension induced by endotoxin or PAF (Eur. J. Pharmacol., 135, 117–122 (1987)). In addition, it was reported that apafant completely prevented any increase in airway resistance after PAF inhalation and inhibited development of cardiovascular and side effects induced by PAF in double-blind clinical pharmacological tests (Clin. Pharmacol. Ther., 47, 456–462 (1990)).

As ophthalmic application, WO91/18608 discloses that apafant can also be used in eyes etc. topically as an antipruritic because it inhibits an itching-inducing activity of PAF. However, it does not disclose an aqueous ophthalmic solution containing apafant as an active ingredient.

Thus, stability of apafant in an aqueous ophthalmic solution is discussed in order to develop the aqueous ophthalmic solution containing apafant, which is useful as a medicine, i.e., as an active ingredient. However, there exists the problem that a stable aqueous ophthalmic solution of apafant cannot be obtained if the formulation of apafant is attempted using conventional techniques. Accordingly, it is necessary to solve the instability problem of apafant in the aqueous ophthalmic solution in order to develop the aqueous ophthalmic solution containing apafant as the active ingredient.

SUMMARY OF THE INVENTION

The inventors studied extensively in order to provide an aqueous ophthalmic solution containing apafant as the active ingredient and being excellent in stability. As a result, the inventors found out that the aqueous ophthalmic solution which is excellent in stability can be prepared by adjusting ionic strength of the ophthalmic solution to 0.05 or below.

DETAILED DESCRIPTION OF THE INVENTION

The present invention relates to an aqueous ophthalmic solution containing apafant and additives wherein apafant is stabilized by lowering ionic strength to 0.05 or below and a method of stabilizing apafant. (This solution is hereinafter referred to as the present ophthalmic solution.) The additives in the present ophthalmic solution are agents which are usually used in ophthalmic preparations such as pH adjusting agents (e.g. hydrochloric acid, sodium hydroxide); isotonic agents, which have an action to adjust an osmotic pressure ratio, such as nonelectrolytes (e.g. glycerin, propylene glycol, mannitol, glucose) and electrolytes (e.g. sodium chloride, potassium chloride); buffers (e.g. sodium dihydrogenphosphate, disodium hydrogenphosphate, sodium phosphate, sodium acetate); stabilizing agents (e.g. sodium citrate, sodium edetate); and preservatives (e.g. benzalkonium chloride, paraben). One or more of additives can be selected suitably from the above-mentioned additives and used.

The ionic strength is represented by ionic strength of each ionic species (i) of electrolytes originated from the additives in the present ophthalmic solution and is a value calculated according to the following equation.

Total of ionic strength of additive:

$$\mu = \frac{1}{2}\sum_{i=1}^{n} Ci \cdot Zi^2$$

Ci: Molar concentration of ion
Zi: Ionic value

The ionic strength of the present ophthalmic solution can be selected within the range of 0.05 or below. In particular, the ionic strength is preferably 0.005 or below and can be a value which is unlimitedly close to 0.

A concentration of apafant to be used, which is an active ingredient of the present ophthalmic solution, can be selected according to symptoms, and the concentration is preferably 0.01 to 1% (w/v), more preferably 0.1 to 1% (w/v).

In general, when an ophthalmic solution is prepared, it is preferable to adjust pH and an osmotic pressure ratio in ranges which are acceptable to ophthalmic preparations. The pH is adjusted using the pH adjusting agent such as hydrochloric acid or sodium hydroxide, or phosphate buffer. The osmotic pressure ratio is usually adjusted using the electrolytic isotonic agent such as sodium chloride. However, a solution containing no isotonic agent can also be used as the ophthalmic solution.

In order to adjust the osmotic pressure ratio of the present ophthalmic solution, it is preferable to add an isotonic agent which is a nonelectrolyte such as glycerin, propylene glycol, mannitol or glucose, which does not participate in the ionic strength. A particularly preferred isotonic agent is glycerin (for example, glycerin or concentrated glycerin defined in Japanese pharmacopeia) among the nonelectrolytic isotonic agents. An ophthalmic solution containing glycerin at a concentration of 1.2 to 3.0% (w/v) is preferable. The osmotic pressure ratio can be adjusted in the range which is acceptable to the ophthalmic preparations and is preferably in a range of 0.5 to 2.0.

It was reported that apafant, which is an antagonist to PAF, is useful for osteoporosis (WO93/07129), cardiopathy such as heart failure (Japanese Laid-open Patent Publication No. 106826/1991) and autoimmune diseases (WO90/01927), increased survival rates against anaphylactic shock (J. Pharmacol. Exp. Ther., 260, 748–755 (1992)), exhibited antagonism to hypotension induced by endotoxin or PAF (Eur. J. Pharmacol., 135, 117–122 (1987)), prevented any increase in airway resistance after PAF inhalation and development of cardiovascular and side effects induced by PAF (Clin. Pharmacol.

Ther., 47, 456–462 (1990)), etc.

As an ophthalmic application, the use of apafant in eyes as an antipruritic is disclosed (WO91/18608). However, there exists the problem that an ophthalmic preparation had a defect in stability.

Then, the inventors studied extensively in order to provide an aqueous ophthalmic solution containing apafant which is excellent in stability. Since apafant is a substance which is hardly soluble in water, it cannot be formulated into the aqueous ophthalmic solution without special devising.

1) First, the inventors noted that apafant is a basic substance and studied a method wherein it is dissolved in an acid and then pH is adjusted with alkali as the most general method. In a first attempt, apafant was dissolved in hydrochloric acid and then pH was adjusted with sodium hydroxide, and an osmotic pressure was adjusted by adding sodium chloride, which is an electrolyte, as the isotonic agent. However, decomposition of apafant was observed and satisfactory stability could not be obtained in the preparation. Therefore, studying the stability of apafant by using glycerin, which is a nonelectrolyte, as the isotonic agent, no decomposition of apafant was observed. 2) Further, studying extensively, apafant was found to be soluble in hot water, crystals thereof are not precipitated even if the resulting solution is cooled to room temperature, and apafant can exist stably in the solution. Preparations of aqueous ophthalmic solutions were studied on the basis of the above findings. It was found that a stable aqueous ophthalmic solution can be obtained by dissolving apafant in hot water, cooling the resulting solution to room temperature and adding a pH adjusting agent (buffer agent) and an isotonic agent thereto in required amounts.

Analyzing the findings of 1) and 2), it was found that ionic strength of the aqueous ophthalmic solution containing apafant as the active ingredient influences the stability of apafant greatly and stable aqueous ophthalmic solutions can be obtained by lowering the ionic strength. In addition, it was found that the ionic strength of the ophthalmic solution must be 0.05 or below. In particular, a preferred value is 0.005 or below.

The present invention is basically based on the ideas of above 1) and 2).

First, according to the above idea 1), an aqueous solution is prepared by the method wherein apafant is dissolved in the acid and the resulting solution is neutralized with the alkali. In this case, the ionic strength approaches the allowable upper limit at the step of neutralization. However, the desired stable aqueous ophthalmic solution can be obtained by adding glycerin, propylene glycol, mannitol, glucose or a like, which is the nonelectrolyte, as the isotonic agent thereto.

Next, according to the above idea 2), an aqueous solution is prepared by the method wherein apafant is dissolved in hot water, and the pH adjusting agent and the isotonic agent are added to the resulting solution. In this case, ionic strength is not produced at the dissolving step of apafant and a degree of freedom is fairly allowed for subsequent operation. Accordingly, there can be used not only glycerin, propylene glycol, mannitol, glucose or a like, which is the nonelectrolyte, but also sodium chloride, potassium chloride or the like, which is an electrolyte, as the isotonic agent.

It is also possible to add a buffer such as sodium dihydrogenphosphate, disodium hydrogenphosphate, sodium phosphate or sodium acetate, a stabilizing agent such as sodium citrate or sodium edetate, preservatives such as benzalkonium chloride or paraben, etc. in required amounts, if necessary, after dissolving apafant in the above-mentioned methods of preparation. These agents must be added so that ionic strength of the resulting ophthalmic solution is 0.05 or below. In addition, pH of the present ophthalmic solution can be in the range which is acceptable to the ophthalmic preparations and is preferably in a range of 4 to 8.

BEST MODE FOR CARRYING OUT THE INVENTION

Examples of the formulation of the present ophthalmic solution are shown below, and they are intended for better understanding the present invention but are not to limit the scope of the present invention.

EXAMPLE 1

Apafant (1 g) was added to 0.1N hydrochloric acid (45 ml) while stirring to completely dissolve it. To the solution was added 0.1N sodium hydroxide (45 ml), and the mixture was stirred. A trace amount of hydrochloric acid or sodium hydroxide was added thereto to adjust pH to 7.4, and then sterile purified water was added thereto to a total volume of 100 ml. The resulting colorless and clear aqueous solution was finally filtered and sterilized to prepare a 1% (w/v) aqueous apafant ophthalmic solution (ionic strength: $\mu$=ca. 0.045).

EXAMPLE 2

To the ophthalmic solution obtained in Example 1 was added 1.8 g of glycerin (concentrated glycerin according to Japanese pharmacopeia) for adjusting osmotic pressure ratio to give an aqueous ophthalmic solution (ionic strength: $\mu$=ca. 0.045).

EXAMPLE 3

Apafant (1 g) was added to 0.1N hydrochloric acid (45 ml) while stirring to completely dissolve it. To the solution were added 0.1N sodium hydroxide (45 ml), glycerin (concentrated glycerin according to Japanese pharmacopeia) (1.8 g) and benzalkonium chloride (5 mg), and the mixture was stirred. A trace amount of hydrochloric acid or sodium hydroxide was added thereto to adjust 1pH to 7.4, and then sterile purified water was added thereto to a total volume of 100 ml. The resulting colorless and clear solution was finally filtered and sterilized to prepare a 1% (w/v) aqueous apafant ophthalmic solution (ionic strength: $\mu$=ca. 0.045).

EXAMPLE 4

A 0.1% (w/v) aqueous apafant ophthalmic solution (ionic strength: $\mu$=ca. 0.045) was prepared by a method similar to Example 3.

EXAMPLE 5

Apafant (1 g) was added to sterile purified water at 70 to 80° C. (70 ml) while stirring to completely dissolve it. The resulting aqueous solution was allowed to stand at room temperature to cool it. A trace amount of hydrochloric acid or sodium hydroxide was added thereto to adjust pH to 7.4, and then sterile purified water was added thereto to a total volume of 100 ml. The resulting colorless and clear aqueous solution was finally filtered and sterilized to prepare a 1% (w/v) aqueous apafant ophthalmic solution (ionic strength: $\mu$=ca. 0).

EXAMPLE 6

To the ophthalmic solution obtained in Example 5 was added 2.6 g of glycerin (concentrated glycerin according to Japanese pharmacopeia) for adjusting osmotic pressure ratio to give an aqueous ophthalmic solution (ionic strength: $\mu$=ca. 0).

EXAMPLE 7

Apafant (1 g) was added to sterile purified water at 70 to 80° C. (70 ml) while stirring to completely dissolve it. The resulting aqueous solution was allowed to stand at room temperature to cool it. To this were added glycerin (concentrated glycerin according to Japanese pharmacopeia) (2.5 g), sodium dihydrogenphosphate dihydrate (50 mg) and benzalkonium chloride (5 mg), and they were dissolved. A trace amount of hydrochloric acid or sodium hydroxide was added thereto to adjust pH to 6.0, and then sterile purified water was added thereto to a total volume of 100 ml. The resulting colorless and clear solution was finally filtered and sterilized to prepare a 1% (w/v) aqueous apafant ophthalmic solution (ionic strength: $\mu$=ca. 0.003).

EXAMPLE 8

A 0.1% (w/v) aqueous apafant ophthalmic solution (ionic strength: $\mu$=ca. 0.003) was prepared by a method similar to Example 7.

Components of each Example are expressed in % by weight (w/v), %by volume (v/v) or molar concentration (M) in Table 1.

TABLE 1

| Example No. | 1 | 2 | 3 | 4 | 5 | 6 | 7 | 8 |
|---|---|---|---|---|---|---|---|---|
| Apafant | 1% | 1% | 1% | 0.1% | 1% | 1% | 1% | 0.1% |
| 0.1 N HCl[a] | 45% | 45% | 45% | 45% | Trace amount | Trace amount | Trace amount | Trace amount |
| 0.1 N NaOH[b] | 45% | 45% | 45% | 45% | Trace amount | Trace amount | Trace amount | Trace amount |
| Glycerin[c] | — | 1.8% | 1.8% | 1.8% | — | 2.6% | 2.5% | 2.5% |
| $NaH_2PO_4 \cdot 2H_2O$[d] | — | — | — | — | — | — | 3.2 mM | 3.2 mM |
| Benzalkonium chloride | — | — | 0.15 mM | 0.15 mM | — | — | 0.15 mM | 0.15 mM |
| pH | 7.4 | 7.4 | 7.4 | 7.4. | 7.4 | 7.4 | 6.0 | 6.0 |
| Ionic strength: $\mu$ | 0.045 | 0.045 | 0.045 | 0.045 | 0 | 0 | 0.003 | 0.003 |

[a] Hydrochloric acid
[b] Sodium hydroxide
[c] Concentrated glycerin according to Japanese pharmacopeia
[d] Sodium dihydrogenphosphate dihydrate Comparative Example 1

Apafant (1 g) was added to 0.1N hydrochloric acid (45 ml) while stirring to completely dissolve it. To the solution were added 0.1N sodium hydroxide (45 ml) and sodium chloride (153 mg), and the mixture was stirred. A trace amount of hydrochloric acid or sodium hydroxide was added thereto to adjust pH to 7.4, and then sterile purified water was added thereto to a total volume of 100 ml. The resulting colorless and clear solution was finally filtered and sterilized to prepare a 1% (w/v) aqueous apafant ophthalmic solution (ionic strength: $\mu$=ca. 0.071).

Comparative Example 2

Apafant (1 g) was added to 0.1N hydrochloric acid (45 ml) while stirring to completely dissolve it. To the solution were added 0.1N sodium hydroxide (45 ml) and disodium hydrogenphosphate dodecahydrate (358 mg), and the mixture was stirred. A trace amount of hydrochloric acid or sodium hydroxide was added thereto to adjust pH to 7.4, and then sterile purified water was added thereto to a total volume of 100 ml. The resulting colorless and clear solution was finally filtered and sterilized to prepare a 1% (w/v) aqueous apafant ophthalmic solution (ionic strength: $\mu$=ca. 0.075).

Comparative Example 3

Apafant (1 g) was added to 0.1N hydrochloric acid (45 ml) while stirring to completely dissolve it. To the solution were added 0.1N sodium hydroxide (45 ml) and disodium hydrogenphosphate dodecahydrate (3.58 g), and the mixture was stirred. A trace amount of hydrochloric acid or sodium hydroxide was added thereto to adjust pH to 7.4, and then sterile purified water was added thereto to a total volume of 100 ml. The resulting colorless and clear solution was finally filtered and sterilized to prepare a 1% (w/v) aqueous apafant ophthalmic solution (ionic strength: $\mu$=ca. 0.345).

Components of each Comparative Example are expressed in % by weight (w/v), %by volume (v/v) or molar concentration (M) in Table 2.

TABLE 2

|  | Comparative Example 1 | Comparative Example 2 | Comparative Example 3 |
|---|---|---|---|
| Apafant | 1% | 1% | 1% |
| 0.1 N HCl[a)] | 45% | 45% | 45% |
| 0.1 N NaOH[b)] | 45% | 45% | 45% |
| Sodium chloride | 0.026 M | — | — |
| $Na_2HPO_4 \cdot 12H_2O$[d)] | — | 0.01 M | 0.1 M |
| pH | 7.4 | 7.4 | 7.4 |
| Ionic strength: $\mu$ | 0.071 | 0.075 | 0.345 |

[a)]Hydrochloric acid
[b)]Sodium hydroxide
[d)]Disodium hydrogenphosphate dodecahydrate Preparation Property Test Stability test (Effect of ionic strength on remaining rate of apafant)

A remaining rate of apafant, which is an active ingredient, was studied by the following method in order to study stability of the present ophthalmic solution.

Experimental Method

A glass vessel was packed with a test preparation, which was preserved at 80° C. for three, six and fourteen days, and an amount of apafant in the preparation was determined by high performance liquid chromatography.

Results

Table 3 shows remaining rates of apafant in 1% (w/v) aqueous apafant ophthalmic solutions having verious ionic strength as some examples of experimental results.

TABLE 3

|  | Remaining rate (%) | | |
|---|---|---|---|
|  | 3 days | 6 days | 14 days |
| Example 5 ($\mu$ = ca. 0) | 100.3 | 98.4 | 99.8 |
| Example 7 ($\mu$ = ca. 0.003) | 99.6 | 98.9 | 97.2 |
| Example 1 ($\mu$ = ca. 0.045) | 95.9 | 94.5 | 93.0 |
| Comparative Example 1 ($\mu$ = ca. 0.071) | 96.6 | 89.5 | 73.1 |
| Comparative Example 2 ($\mu$ = ca. 0.075) | 88.5 | 74.3 | — |
| Comparative Example 3 ($\mu$ = ca. 0.345) | 75.7 | 51.4 | — |

—Not carried out

As shown in Table 3, decomposition of apafant was promoted with an increase in ionic strength. However, the remaining rates of apafant were 93% or more in the preparations having ionic strengths of 0.045 or below even if the preparations were preserved under the above-mentioned stress condition for 14 days. In particular, the remaining rates of apafant were 97% or more in the preparations having ionic strengths of 0.003 or below after the preparations were preserved for 14 days, and no influence of the ionic strength on the remaining rate of apafant was recognized in such cases.

From the above-mentioned results, the present ophthalmic solution was recognized to be an ophthalmic solution being excellent in stability and be useful as an aqueous ophthalmic solution containing apafant as an active ingredient.

Industrial Applicability

The present invention relates to an aqueous ophthalmic solution containing apafant as an active ingredient and a method for attaining stabilization of apafant in the aqueous ophthalmic solution by lowering ionic strength (0.05 or below) depending on additives contained in the solution.

We claim:

1. A stable aqueous ophthalmic solution comprising apafant and an additive, said additive being in an amount sufficient to adjust the ionic strength of the solution to 0.05 or below.

2. The aqueous ophthalmic solution as claimed in claim 1, wherein the ionic strength is 0.005 or below.

3. The aqueous ophthalmic solution as claimed in claim 1 or 2, wherein the apafant is in a concentration of 0.01 to 1% (w/v).

4. The aqueous ophthalmic solution as claimed in claim 1 or 2, wherein the apafant is in a concentration of 0.1 to 1% w/v).

5. The aqueous ophthalmic solution as claimed in claim 1 or 2, wherein the additive is a nonelectrolytic isotonic agent.

6. The aqueous ophthalmic solution as claimed in claim 5, wherein the nonelectrolytic isotonic agent is glycerin, propylene glycol, mannitol or glucose.

7. The aqueous ophthalmic solution as claimed in claim 5, wherein the nonelectrolytic isotonic agent is glycerin.

8. The aqueous ophthalmic solution as claimed in claim 7, wherein the glycerin is in a concentration of 1.2 to 3.0% (w/v).

9. A method of stabilizing apafant in an aqueous ophthalmic solution containing apafant comprising adding to the solution an additive in a sufficient amount for adjusting the ionic strength of the solution to 0.05 or below.

10. The method of stabilizing apafant as claimed in claim 9, wherein the ionic strength is adjusted to 0.005 or below.

11. The method of stabilizing apafant as claimed in claim 9 or 10, wherein the solution contains apafant in a concentration of 0.01 to 1% (w/v).

12. The method of stabilizing apafant as claimed in claim 9 or 10, wherein the solution contains apafant in a concentration of 0.1 to 1% (w/v).

13. The method of stabilizing apafant as claimed in claim 9 or 10, wherein the additive is a nonelectrolytic isotonic agent.

14. The method of stabilizing apafant as claimed in claim 13, wherein the nonelectrolytic isotonic agent is glycerin, propylene glycol, mannitol or glucose.

15. The method of stabilizing apafant as claimed in claim 13, wherein the nonelectrolytic isotonic agent is glycerin.

16. The method of stabilizing apafant as claimed in claim 15, wherein the glycerin is in a concentration of 1.2 to 3.0% (w/v).

17. The aqueous ophthalmic solution as claimed in claim 3, wherein the additive is a nonelectrolytic isotonic agent.

18. The aqueous ophthalmic solution as claimed in claim 4, wherein the additive is a nonelectrolytic isotonic agent.

19. The aqueous ophthalmic solution as claimed in claim 17, wherein the nonelectrolytic isotonic agent is glycerin, propylene glycol, mannitol or glucose.

20. The aqueous ophthalmic solution as claimed in claim 18, wherein the nonelectrolytic isotonic agent is glycerin, propylene glycol, mannitol or glucose.

21. The aqueous ophthalmic solution as claimed in claim 17, wherein the nonelectrolytic isotonic agent is glycerin.

22. The aqueous ophthalmic solution as claimed in claim 18, wherein the nonelectrolytic isotonic agent is glycerin.

23. The aqueous ophthalmic solution as claimed in claim 21, wherein the glycerin is in a concentration of 1.2 to 3.0 (w/v).

24. The aqueous ophthalmic solution as claimed in claim 22, wherein the glycerin is in a concentration of 1.2 to 3.0% (w/v).

25. The method of stabilizing apafant as claimed in claim 11, wherein the additive is a nonelectrolytic isotonic agent.

26. The method of stabilizing apafant as claimed in claim 12, wherein the additive is a nonelectrolytic isotonic agent.

27. The method of stabilizing apafant as claimed in claim 25, wherein the nonelectrolytic isotonic agent is glycerin, propylene glycol, mannitol or glucose.

28. The method of stabilizing apafant as claimed in claim 26, wherein the nonelectrolytic isotonic agent is glycerin, propylene glycol, mannitol or glucose.

29. The method of stabilizing apafant as claimed in claim 25, wherein the nonelectrolytic isotonic agent is glycerin.

30. The method of stabilizing apafant as claimed in claim 26, wherein the nonelectrolytic isotonic agent is glycerin.

31. The method of stabilizing apafant as claimed in claim 29, wherein the glycerin is in a concentration of 1.2 to 3.0% (w/v).

32. The method of stabilizing apafant as claimed in claim 30, wherein the glycerin is in a concentration of 1.2 to 3.0% (w/v).

* * * * *